(12) United States Patent
Kobunai et al.

(10) Patent No.: US 9,345,767 B2
(45) Date of Patent: May 24, 2016

(54) METHOD FOR SELECTING CHEMOTHERAPY FOR GASTRIC CANCER PATIENT USING COMBINATION DRUG OF TEGAFUR, GIMERACIL AND OTERACIL POTASSIUM AND EGFR INHIBITOR

(75) Inventors: Takashi Kobunai, Tokyo (JP); Hitoshi Saito, Tokushima (JP); Teiji Takechi, Tokyo (JP)

(73) Assignee: TAIHO PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/117,426

(22) PCT Filed: May 15, 2012

(86) PCT No.: PCT/JP2012/062423
§ 371 (c)(1),
(2), (4) Date: Jan. 2, 2014

(87) PCT Pub. No.: WO2012/157647
PCT Pub. Date: Nov. 22, 2012

(65) Prior Publication Data
US 2014/0105893 A1    Apr. 17, 2014

(30) Foreign Application Priority Data

May 16, 2011   (JP) .................................. 2011-109599

(51) Int. Cl.
| | |
|---|---|
| *A61K 39/395* | (2006.01) |
| *G01N 33/574* | (2006.01) |
| *C12Q 1/68* | (2006.01) |
| *A61K 45/06* | (2006.01) |
| *A61K 31/4412* | (2006.01) |
| *A61K 31/513* | (2006.01) |
| *A61K 31/53* | (2006.01) |
| *C07K 16/28* | (2006.01) |
| *A61K 39/00* | (2006.01) |

(52) U.S. Cl.
CPC ....... *A61K 39/39558* (2013.01); *A61K 31/4412* (2013.01); *A61K 31/513* (2013.01); *A61K 31/53* (2013.01); *A61K 45/06* (2013.01); *C07K 16/2863* (2013.01); *C12Q 1/6886* (2013.01); *G01N 33/57446* (2013.01); *A61K 2039/505* (2013.01); *C12Q 2600/106* (2013.01); *C12Q 2600/158* (2013.01); *G01N 2333/485* (2013.01); *G01N 2800/52* (2013.01)

(58) Field of Classification Search
CPC .......................... A61K 39/395; G01N 33/574
USPC .............................. 424/133.1; 435/7.23, 6.12
See application file for complete search history.

(56) References Cited

U.S. PATENT DOCUMENTS

2009/0318453 A1\* 12/2009 Okabe .......................... 514/241

FOREIGN PATENT DOCUMENTS

| WO | 2007050495 A2 | 5/2007 |
|---|---|---|
| WO | 2010074240 A1 | 7/2010 |

OTHER PUBLICATIONS

Sirak et al. (Strahlenther Onkol., 2008, 184: 592-7).\*
Han et al. (British Journal of Cancer, 2009, 100: 298-304).\*
Hosaka et al., Shin' yaku Profile File [12], Erbitax Chushaeki 100mg, Shukan Yakuji Shinpo, 2009, No. 2595, pp. 1000-10004 (Abstract).
Hara et al., "Interleukin-2 potentiation of cetuximab antitumor activity for epidermal growth factor receptor-overexpressing gastric cancer xenografts through antibody-dependent cellular cytotoxicity", Cancer Science, 2008, vol. 99, No. 7, pp. 1471-1478.
Cascone et al., "Synergistic anti-prolifereatie and pro-apoptotic activity of combined therapy with bortezomib, a proteasome inhibitor, with anti-epidermal growth factor receptor (EGFR) drugs in human cancer cells", Journal of Cellular Physiology, 2008, vol. 216, No. 3, pp. 698-707.
Kuwakado et al., "Chemotherapy of gastric cancer has come a long way", The Journal of Adult Diseases, 2007, vol. 37, No. 6, pp. 657-662 (English Abstract).
Muro et al., "Cancer in the Digestive System", Saishin Igaku, 2007, vol. 62, the March Special Extra Issue, pp. 671-682 (English Abstract).
Machida et al., "Standard chemotherapy for colon cancer", The Japanese Journal of Nursing Arts, 2008, vol. 54, No. 4, pp. 322-332 (English Abstract).

(Continued)

*Primary Examiner* — Yan Xiao
(74) *Attorney, Agent, or Firm* — Rothwell, Figg, Ernst & Manbeck, P.C.

(57) ABSTRACT

A method for predicting a therapeutic effect of chemotherapy with a combination drug containing tegafur, gimeracil, and oteracil potassium in a gastric cancer patient by:

(1) measuring an expression level of epidermal growth factor receptor (EGFR) in a biological sample obtained from the patient;
(2) comparing the expression level of EGFR obtained in step (1) with a corresponding predetermined cut-off point; and
(3) predicting that the patient is likely to sufficiently respond to chemotherapy when a tegafur, gimeracil, and oteracil potassium combination drug is used with an EGFR inhibitor, when the step (2) comparison reveals that the expression level of EGFR is greater than the cut-off point, or predicting that the patient is likely to sufficiently respond to chemotherapy when a tegafur, gimeracil, and oteracil potassium combination drug is used alone, when the step (2) comparison reveals that the expression level of EGFR is not greater than the cut-off point.

9 Claims, 8 Drawing Sheets

(56) References Cited

OTHER PUBLICATIONS

Sakuramoto et al., "Adjuvant Chemotherapy for Gastric Cancer with S-1, an Oral Fluoropyrimidine", The New England Journal of Medicine, 2007, vol. 357, No. 18, pp. 1810-1820.

International Search Report dated Jul. 10, 2012, in PCT/JP2012/062423 (5 pgs).

Kazumas Fukuda, Antitumor effect of cetuximab in combination with S-1 in EGFR-amplified gastric cancer cells, International Journal of Oncology, 40, 2012, pp. 975-982.

S-W Han et al., Phase II study and biomarker analysis of cetuximab combined with modified FOLFOX6 in advanced gastric cancer, British Journal of Cancer, vol. 100, No. 2, 2009, pp. 298-304.

Junichi Matsubara et al., Clinical significance of insulin-like growth factor type 1 receptor and epidermal growth factor receptor in patients with advanced gastric cancer, Oncology, vol. 74, No. 1-2, 2008, pp. 76-83.

J. Matsubara et al., Impacts of excision repair cross-complementing gene 1 (ERCC1), dihydropyrimidine dehydrogenase, and epidermal growth factor receptor on the outcomes of patients with advanced gastric cancer, British Journal of Cancer, vol. 98, No. 4, 2008, pp. 832-839.

Sook Ryun Park et al., Predictive factors for the efficacy of cetuximab plus chemotherapy as salvage therapy in metastatic gastric cancer patients, Cancer Chemotherapy and Pharmacology, vol. 65, No. 3, 2010, pp. 579-587.

Extended European Search Report dated Nov. 19, 2014 for the corresponding EP Patent Application No. 12785253.1.

* cited by examiner

SEQUENCE LISTING

```
<160> NUMBER OF SEQ ID NOS: 2

<210> SEQ ID NO 1
<211> LENGTH: 5616
<212> TYPE: DNA
<213> ORGANISM: Homo sapiens
<220> FEATURE:
<221> NAME/KEY: CDS
<222> LOCATION: (247)..(3879)

<400> SEQUENCE: 1
ccccggcgca gcgcggccgc agcagcctcc gcccccgca cggtgtgagc gcccgacgcg      60
gccgaggcgg ccggagtccc gagctagccc cggcggccgc cgccgcccag accggacgac     120
aggccacctc gtcggcgtcc gcccgagtcc ccgcctcgcc gccaacgcca caaccaccgc     180
gcacggcccc ctgactccgt ccagtattga tcgggagagc cggagcgagc tcttcgggga     240 gcagcg atg cga ccc tcc ggg acg gcc ggg gca gcg ctc ctg gcg ctg        288
       Met Arg Pro Ser Gly Thr Ala Gly Ala Ala Leu Leu Ala Leu
         1               5                  10 ctg gct gcg ctc tgc ccg gcg agt cgg gct ctg gag gaa aag aaa gtt       336
Leu Ala Ala Leu Cys Pro Ala Ser Arg Ala Leu Glu Glu Lys Lys Val
```

-continued

|  |  |  |  |  |  |  |  |  |  |  |  |  |  |  |  |
|---|---|---|---|---|---|---|---|---|---|---|---|---|---|---|---|

```
                15                  20                  25                  30
        tgc caa ggc acg agt aac aag ctc acg cag ttg ggc act ttt gaa gat      384
        Cys Gln Gly Thr Ser Asn Lys Leu Thr Gln Leu Gly Thr Phe Glu Asp
                         35                  40                  45 cat ttt ctc agc ctc cag agg atg ttc aat aac tgt gag gtg gtc ctt      432
        His Phe Leu Ser Leu Gln Arg Met Phe Asn Asn Cys Glu Val Val Leu
                 50                  55                  60 ggg aat ttg gaa att acc tat gtg cag agg aat tat gat ctt tcc ttc      480
        Gly Asn Leu Glu Ile Thr Tyr Val Gln Arg Asn Tyr Asp Leu Ser Phe
                 65                  70                  75 tta aag acc atc cag gag gtg gct ggt tat gtc ctc att gcc ctc aac      528
        Leu Lys Thr Ile Gln Glu Val Ala Gly Tyr Val Leu Ile Ala Leu Asn
             80                  85                  90 aca gtg gag cga att cct ttg gaa aac ctg cag atc atc aga gga aat      576
        Thr Val Glu Arg Ile Pro Leu Glu Asn Leu Gln Ile Ile Arg Gly Asn
         95                 100                 105                 110 atg tac tac gaa aat tcc tat gcc tta gca gtc tta tct aac tat gat      624
        Met Tyr Tyr Glu Asn Ser Tyr Ala Leu Ala Val Leu Ser Asn Tyr Asp
                        115                 120                 125 gca aat aaa acc gga ctg aag gag ctg ccc atg aga aat tta cag gaa      672
        Ala Asn Lys Thr Gly Leu Lys Glu Leu Pro Met Arg Asn Leu Gln Glu
                    130                 135                 140 atc ctg cat ggc gcc gtg cgg ttc agc aac aac cct gcc ctg tgc aac      720
        Ile Leu His Gly Ala Val Arg Phe Ser Asn Asn Pro Ala Leu Cys Asn
                145                 150                 155 gtg gag agc atc cag tgg cgg gac ata gtc agc agt gac ttt ctc agc      768
        Val Glu Ser Ile Gln Trp Arg Asp Ile Val Ser Ser Asp Phe Leu Ser
                160                 165                 170 aac atg tcg atg gac ttc cag aac cac ctg ggc agc tgc caa aag tgt      816
        Asn Met Ser Met Asp Phe Gln Asn His Leu Gly Ser Cys Gln Lys Cys
        175                 180                 185                 190 gat cca agc tgt ccc aat ggg agc tgc tgg ggt gca gga gag gag aac      864
        Asp Pro Ser Cys Pro Asn Gly Ser Cys Trp Gly Ala Gly Glu Glu Asn
                        195                 200                 205 tgc cag aaa ctg acc aaa atc atc tgt gcc cag cag tgc tcc ggg cgc      912
        Cys Gln Lys Leu Thr Lys Ile Ile Cys Ala Gln Gln Cys Ser Gly Arg
                    210                 215                 220 tgc cgt ggc aag tcc ccc agt gac tgc tgc cac aac cag tgt gct gca      960
        Cys Arg Gly Lys Ser Pro Ser Asp Cys Cys His Asn Gln Cys Ala Ala
                225                 230                 235 ggc tgc aca ggc ccc cgg gag agc gac tgc ctg gtc tgc cgc aaa ttc     1008
        Gly Cys Thr Gly Pro Arg Glu Ser Asp Cys Leu Val Cys Arg Lys Phe
                240                 245                 250 cga gac gaa gcc acg tgc aag gac acc tgc ccc cca ctc atg ctc tac     1056
        Arg Asp Glu Ala Thr Cys Lys Asp Thr Cys Pro Pro Leu Met Leu Tyr
        255                 260                 265                 270 aac ccc acc acg tac cag atg gat gtg aac ccc gag ggc aaa tac agc     1104
        Asn Pro Thr Thr Tyr Gln Met Asp Val Asn Pro Glu Gly Lys Tyr Ser
                        275                 280                 285 ttt ggt gcc acc tgc gtg aag aag tgt ccc cgt aat tat gtg gtg aca     1152
        Phe Gly Ala Thr Cys Val Lys Lys Cys Pro Arg Asn Tyr Val Val Thr
                    290                 295                 300 gat cac ggc tcg tgc gtc cga gcc tgt ggg gcc gac agc tat gag atg     1200
        Asp His Gly Ser Cys Val Arg Ala Cys Gly Ala Asp Ser Tyr Glu Met
                305                 310                 315 gag gaa gac ggc gtc cgc aag tgt aag aag tgc gaa ggg cct tgc cgc     1248
        Glu Glu Asp Gly Val Arg Lys Cys Lys Lys Cys Glu Gly Pro Cys Arg
        320                 325                 330 aaa gtg tgt aac gga ata ggt att ggt gaa ttt aaa gac tca ctc tcc     1296
```

|  |  |
|---|---|
| Lys Val Cys Asn Gly Ile Gly Ile Gly Glu Phe Lys Asp Ser Leu Ser<br>335                    340                    345                    350 |  |
| ata aat gct acg aat att aaa cac ttc aaa aac tgc acc tcc atc agt<br>Ile Asn Ala Thr Asn Ile Lys His Phe Lys Asn Cys Thr Ser Ile Ser<br>                    355                    360                    365 | 1344 |
| ggc gat ctc cac atc ctg ccg gtg gca ttt agg ggt gac tcc ttc aca<br>Gly Asp Leu His Ile Leu Pro Val Ala Phe Arg Gly Asp Ser Phe Thr<br>              370                    375                    380 | 1392 |
| cat act cct cct ctg gat cca cag gaa ctg gat att ctg aaa acc gta<br>His Thr Pro Pro Leu Asp Pro Gln Glu Leu Asp Ile Leu Lys Thr Val<br>        385                    390                    395 | 1440 |
| aag gaa atc aca ggg ttt ttg ctg att cag gct tgg cct gaa aac agg<br>Lys Glu Ile Thr Gly Phe Leu Leu Ile Gln Ala Trp Pro Glu Asn Arg<br>400                    405                    410 | 1488 |
| acg gac ctc cat gcc ttt gag aac cta gaa atc ata cgc ggc agg acc<br>Thr Asp Leu His Ala Phe Glu Asn Leu Glu Ile Ile Arg Gly Arg Thr<br>415                    420                    425                    430 | 1536 |
| aag caa cat ggt cag ttt tct ctt gca gtc gtc agc ctg aac ata aca<br>Lys Gln His Gly Gln Phe Ser Leu Ala Val Val Ser Leu Asn Ile Thr<br>                    435                    440                    445 | 1584 |
| tcc ttg gga tta cgc tcc ctc aag gag ata agt gat gga gat gtg ata<br>Ser Leu Gly Leu Arg Ser Leu Lys Glu Ile Ser Asp Gly Asp Val Ile<br>              450                    455                    460 | 1632 |
| att tca gga aac aaa aat ttg tgc tat gca aat aca ata aac tgg aaa<br>Ile Ser Gly Asn Lys Asn Leu Cys Tyr Ala Asn Thr Ile Asn Trp Lys<br>        465                    470                    475 | 1680 |
| aaa ctg ttt ggg acc tcc ggt cag aaa acc aaa att ata agc aac aga<br>Lys Leu Phe Gly Thr Ser Gly Gln Lys Thr Lys Ile Ile Ser Asn Arg<br>480                    485                    490 | 1728 |
| ggt gaa aac agc tgc aag gcc aca ggc cag gtc tgc cat gcc ttg tgc<br>Gly Glu Asn Ser Cys Lys Ala Thr Gly Gln Val Cys His Ala Leu Cys<br>495                    500                    505                    510 | 1776 |
| tcc ccc gag ggc tgc tgg ggc ccg gag ccc agg gac tgc gtc tct tgc<br>Ser Pro Glu Gly Cys Trp Gly Pro Glu Pro Arg Asp Cys Val Ser Cys<br>                    515                    520                    525 | 1824 |
| cgg aat gtc agc cga ggc agg gaa tgc gtg gac aag tgc aac ctt ctg<br>Arg Asn Val Ser Arg Gly Arg Glu Cys Val Asp Lys Cys Asn Leu Leu<br>                    530                    535                    540 | 1872 |
| gag ggt gag cca agg gag ttt gtg gag aac tct gag tgc ata cag tgc<br>Glu Gly Glu Pro Arg Glu Phe Val Glu Asn Ser Glu Cys Ile Gln Cys<br>        545                    550                    555 | 1920 |
| cac cca gag tgc ctg cct cag gcc atg aac atc acc tgc aca gga cgg<br>His Pro Glu Cys Leu Pro Gln Ala Met Asn Ile Thr Cys Thr Gly Arg<br>560                    565                    570 | 1968 |
| gga cca gac aac tgt atc cag tgt gcc cac tac att gac ggc ccc cac<br>Gly Pro Asp Asn Cys Ile Gln Cys Ala His Tyr Ile Asp Gly Pro His<br>575                    580                    585                    590 | 2016 |
| tgc gtc aag acc tgc ccg gca gga gtc atg gga gaa aac aac acc ctg<br>Cys Val Lys Thr Cys Pro Ala Gly Val Met Gly Glu Asn Asn Thr Leu<br>                    595                    600                    605 | 2064 |
| gtc tgg aag tac gca gac gcc ggc cat gtg tgc cac ctg tgc cat cca<br>Val Trp Lys Tyr Ala Asp Ala Gly His Val Cys His Leu Cys His Pro<br>              610                    615                    620 | 2112 |
| aac tgc acc tac gga tgc act ggg cca ggt ctt gaa ggc tgt cca acg<br>Asn Cys Thr Tyr Gly Cys Thr Gly Pro Gly Leu Glu Gly Cys Pro Thr<br>        625                    630                    635 | 2160 |
| aat ggg cct aag atc ccg tcc atc gcc act ggg atg gtg ggg gcc ctc<br>Asn Gly Pro Lys Ile Pro Ser Ile Ala Thr Gly Met Val Gly Ala Leu<br>640                    645                    650 | 2208 |

-continued

| | |
|---|---|
| ctc ttg ctg ctg gtg gtg gcc ctg ggg atc ggc ctc ttc atg cga agg<br>Leu Leu Leu Leu Val Val Ala Leu Gly Ile Gly Leu Phe Met Arg Arg<br>655                        660                       665                 670 | 2256 |
| cgc cac atc gtt cgg aag cgc acg ctg cgg agg ctg ctg cag gag agg<br>Arg His Ile Val Arg Lys Arg Thr Leu Arg Arg Leu Leu Gln Glu Arg<br>                     675                       680                     685 | 2304 |
| gag ctt gtg gag cct ctt aca ccc agt gga gaa gct ccc aac caa gct<br>Glu Leu Val Glu Pro Leu Thr Pro Ser Gly Glu Ala Pro Asn Gln Ala<br>                690                       695                     700 | 2352 |
| ctc ttg agg atc ttg aag gaa act gaa ttc aaa aag atc aaa gtg ctg<br>Leu Leu Arg Ile Leu Lys Glu Thr Glu Phe Lys Lys Ile Lys Val Leu<br>705                        710                       715 | 2400 |
| ggc tcc ggt gcg ttc ggc acg gtg tat aag gga ctc tgg atc cca gaa<br>Gly Ser Gly Ala Phe Gly Thr Val Tyr Lys Gly Leu Trp Ile Pro Glu<br>        720                     725                     730 | 2448 |
| ggt gag aaa gtt aaa att ccc gtc gct atc aag gaa tta aga gaa gca<br>Gly Glu Lys Val Lys Ile Pro Val Ala Ile Lys Glu Leu Arg Glu Ala<br>735                        740                     745                     750 | 2496 |
| aca tct ccg aaa gcc aac aag gaa atc ctc gat gaa gcc tac gtg atg<br>Thr Ser Pro Lys Ala Asn Lys Glu Ile Leu Asp Glu Ala Tyr Val Met<br>                     755                       760                     765 | 2544 |
| gcc agc gtg gac aac ccc cac gtg tgc cgc ctg ctg ggc atc tgc ctc<br>Ala Ser Val Asp Asn Pro His Val Cys Arg Leu Leu Gly Ile Cys Leu<br>        770                     775                     780 | 2592 |
| acc tcc acc gtg cag ctc atc acg cag ctc atg ccc ttc ggc tgc ctc<br>Thr Ser Thr Val Gln Leu Ile Thr Gln Leu Met Pro Phe Gly Cys Leu<br>785                        790                     795 | 2640 |
| ctg gac tat gtc cgg gaa cac aaa gac aat att ggc tcc cag tac ctg<br>Leu Asp Tyr Val Arg Glu His Lys Asp Asn Ile Gly Ser Gln Tyr Leu<br>        800                     805                     810 | 2688 |
| ctc aac tgg tgt gtg cag atc gca aag ggc atg aac tac ttg gag gac<br>Leu Asn Trp Cys Val Gln Ile Ala Lys Gly Met Asn Tyr Leu Glu Asp<br>815                        820                     825                     830 | 2736 |
| cgt cgc ttg gtg cac cgc gac ctg gca gcc agg aac gta ctg gtg aaa<br>Arg Arg Leu Val His Arg Asp Leu Ala Ala Arg Asn Val Leu Val Lys<br>                     835                       840                     845 | 2784 |
| aca ccg cag cat gtc aag atc aca gat ttt ggg ctg gcc aaa ctg ctg<br>Thr Pro Gln His Val Lys Ile Thr Asp Phe Gly Leu Ala Lys Leu Leu<br>        850                     855                     860 | 2832 |
| ggt gcg gaa gag aaa gaa tac cat gca gaa gga ggc aaa gtg cct atc<br>Gly Ala Glu Glu Lys Glu Tyr His Ala Glu Gly Gly Lys Val Pro Ile<br>865                        870                     875 | 2880 |
| aag tgg atg gca ttg gaa tca att tta cac aga atc tat acc cac cag<br>Lys Trp Met Ala Leu Glu Ser Ile Leu His Arg Ile Tyr Thr His Gln<br>880                        885                     890 | 2928 |
| agt gat gtc tgg agc tac ggg gtg acc gtt tgg gag ttg atg acc ttt<br>Ser Asp Val Trp Ser Tyr Gly Val Thr Val Trp Glu Leu Met Thr Phe<br>895                        900                     905                     910 | 2976 |
| gga tcc aag cca tat gac gga atc cct gcc agc gag atc tcc tcc atc<br>Gly Ser Lys Pro Tyr Asp Gly Ile Pro Ala Ser Glu Ile Ser Ser Ile<br>                     915                       920                     925 | 3024 |
| ctg gag aaa gga gaa cgc ctc cct cag cca ccc ata tgt acc atc gat<br>Leu Glu Lys Gly Glu Arg Leu Pro Gln Pro Pro Ile Cys Thr Ile Asp<br>                     930                       935                     940 | 3072 |
| gtc tac atg atc atg gtc aag tgc tgg atg ata gac gca gat agt cgc<br>Val Tyr Met Ile Met Val Lys Cys Trp Met Ile Asp Ala Asp Ser Arg<br>        945                     950                     955 | 3120 |
| cca aag ttc cgt gag ttg atc atc gaa ttc tcc aaa atg gcc cga gac<br>Pro Lys Phe Arg Glu Leu Ile Ile Glu Phe Ser Lys Met Ala Arg Asp<br>960                        965                     970 | 3168 |

```
ccc cag cgc tac ctt gtc att cag ggg gat gaa aga atg cat ttg cca    3216
Pro Gln Arg Tyr Leu Val Ile Gln Gly Asp Glu Arg Met His Leu Pro
975                 980                 985                 990 agt cct aca gac tcc aac ttc tac cgt gcc ctg atg gat gaa gaa gac    3264
Ser Pro Thr Asp Ser Asn Phe Tyr Arg Ala Leu Met Asp Glu Glu Asp
            995                 1000                1005 atg gac gac gtg gtg gat gcc gac gag tac ctc atc cca cag cag        3309
Met Asp Asp Val Val Asp Ala Asp Glu Tyr Leu Ile Pro Gln Gln
        1010                1015                1020 ggc ttc ttc agc agc ccc tcc acg tca cgg act ccc ctc ctg agc        3354
Gly Phe Phe Ser Ser Pro Ser Thr Ser Arg Thr Pro Leu Leu Ser
        1025                1030                1035 tct ctg agt gca acc agc aac aat tcc acc gtg gct tgc att gat        3399
Ser Leu Ser Ala Thr Ser Asn Asn Ser Thr Val Ala Cys Ile Asp
        1040                1045                1050 aga aat ggg ctg caa agc tgt ccc atc aag gaa gac agc ttc ttg        3444
Arg Asn Gly Leu Gln Ser Cys Pro Ile Lys Glu Asp Ser Phe Leu
        1055                1060                1065 cag cga tac agc tca gac ccc aca ggc gcc ttg act gag gac agc        3489
Gln Arg Tyr Ser Ser Asp Pro Thr Gly Ala Leu Thr Glu Asp Ser
        1070                1075                1080 ata gac gac acc ttc ctc cca gtg cct gaa tac ata aac cag tcc        3534
Ile Asp Asp Thr Phe Leu Pro Val Pro Glu Tyr Ile Asn Gln Ser
        1085                1090                1095 gtt ccc aaa agg ccc gct ggc tct gtg cag aat cct gtc tat cac        3579
Val Pro Lys Arg Pro Ala Gly Ser Val Gln Asn Pro Val Tyr His
        1100                1105                1110 aat cag cct ctg aac ccc gcg ccc agc aga gac cca cac tac cag        3624
Asn Gln Pro Leu Asn Pro Ala Pro Ser Arg Asp Pro His Tyr Gln
        1115                1120                1125 gac ccc cac agc act gca gtg ggc aac ccc gag tat ctc aac act        3669
Asp Pro His Ser Thr Ala Val Gly Asn Pro Glu Tyr Leu Asn Thr
        1130                1135                1140 gtc cag ccc acc tgt gtc aac agc aca ttc gac agc cct gcc cac        3714
Val Gln Pro Thr Cys Val Asn Ser Thr Phe Asp Ser Pro Ala His
        1145                1150                1155 tgg gcc cag aaa ggc agc cac caa att agc ctg gac aac cct gac        3759
Trp Ala Gln Lys Gly Ser His Gln Ile Ser Leu Asp Asn Pro Asp
        1160                1165                1170 tac cag cag gac ttc ttt ccc aag gaa gcc aag cca aat ggc atc        3804
Tyr Gln Gln Asp Phe Phe Pro Lys Glu Ala Lys Pro Asn Gly Ile
        1175                1180                1185 ttt aag ggc tcc aca gct gaa aat gca gaa tac cta agg gtc gcg        3849
Phe Lys Gly Ser Thr Ala Glu Asn Ala Glu Tyr Leu Arg Val Ala
        1190                1195                1200 cca caa agc agt gaa ttt att gga gca tga ccacggagga tagtatgagc      3899
Pro Gln Ser Ser Glu Phe Ile Gly Ala
        1205                1210 cctaaaaatc cagactcttt cgatacccag gaccaagcca cagcaggtcc tccatcccaa  3959
cagccatgcc cgcattagct cttagaccca cagactggtt ttgcaacgtt tacaccgact  4019
agccaggaag tacttccacc tcgggcacat tttgggaagt tgcattcctt tgtcttcaaa  4079
ctgtgaagca tttacagaaa cgcatccagc aagaatattg ccccttgag cagaaattta   4139 tctttcaaag aggtatattt gaaaaaaaaa aaagtatat gtgaggattt ttattgattg    4199
gggatcttgg agttttcat tgtcgctatt gatttttact tcaatgggct cttccaacaa   4259
ggaagaagct tgctggtagc acttgctacc ctgagttcat ccaggcccaa ctgtgagcaa  4319
```

```
ggagcacaag ccacaagtct tccagaggat gcttgattcc agtggttctg cttcaaggct      4379
tccactgcaa aacactaaag atccaagaag gccttcatgg ccccagcagg ccggatcggt      4439
actgtatcaa gtcatggcag gtacagtagg ataagccact ctgtcccttc ctgggcaaag      4499
aagaaacgga ggggatggaa ttcttcctta gacttacttt tgtaaaaatg tccccacggt      4559
acttactccc cactgatgga ccagtggttt ccagtcatga gcgttagact gacttgtttg      4619
tcttccattc cattgttttg aaactcagta tgctgcccct gtcttgctgt catgaaatca      4679
gcaagagagg atgacacatc aaataataac tcggattcca gcccacattg gattcatcag      4739
catttggacc aatagcccac agctgagaat gtggaatacc taaggatagc accgcttttg      4799
ttctcgcaaa aacgtatctc ctaatttgag gctcagatga aatgcatcag gtcctttggg      4859
gcatagatca gaagactaca aaaatgaagc tgctctgaaa tctcctttag ccatcacccc      4919
aaccccccaa aattagtttg tgttacttat ggaagatagt tttctccttt tacttcactt      4979
caaaagcttt ttactcaaag agtatatgtt ccctccaggt cagctgcccc caaaccccct      5039
ccttacgctt tgtcacacaa aaagtgtctc tgccttgagt catctattca agcacttaca      5099
gctctggcca caacagggca ttttacaggt gcgaatgaca gtagcattat gagtagtgtg      5159
gaattcaggt agtaaatatg aaactagggt ttgaaattga taatgctttc acaacatttg      5219
cagatgtttt agaaggaaaa aagttccttc ctaaaataat ttctctacaa ttggaagatt      5279
ggaagattca gctagttagg agcccacctt ttttcctaat ctgtgtgtgc cctgtaacct      5339
gactggttaa cagcagtcct ttgtaaacag tgttttaaac tctcctagtc aatatccacc      5399
ccatccaatt tatcaaggaa gaaatggttc agaaaatatt ttcagcctac agttatgttc      5459
agtcacacac acatacaaaa tgttcctttt gcttttaaag taattttttga ctcccagatc      5519 agtcagagcc cctacagcat tgttaagaaa gtatttgatt tttgtctcaa tgaaaataaa      5579
actatattca tttccactct aaaaaaaaaa aaaaaaa                               5616
```

<210> SEQ ID NO 2
<211> LENGTH: 1210
<212> TYPE: PRT
<213> ORGANISM: Homo sapiens

<400> SEQUENCE: 2

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

```
His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
        165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
        195                 200                 205

Lys Leu Thr Lys Ile Ile Cys Ala Gln Gln Cys Ser Gly Arg Cys Arg
        210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
        290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
        530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
```

```
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
            595                 600                 605
Lys Tyr Ala Asp Ala Gly His Val Cys His Leu Cys His Pro Asn Cys
            610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
                660                 665                 670
Ile Val Arg Lys Arg Thr Leu Arg Arg Leu Leu Gln Glu Arg Glu Leu
                675                 680                 685
Val Glu Pro Leu Thr Pro Ser Gly Glu Ala Pro Asn Gln Ala Leu Leu
            690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
                740                 745                 750
Pro Lys Ala Asn Lys Glu Ile Leu Asp Glu Ala Tyr Val Met Ala Ser
            755                 760                 765
Val Asp Asn Pro His Val Cys Arg Leu Leu Gly Ile Cys Leu Thr Ser
770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
            820                 825                 830
Leu Val His Arg Asp Leu Ala Ala Arg Asn Val Leu Val Lys Thr Pro
            835                 840                 845
Gln His Val Lys Ile Thr Asp Phe Gly Leu Ala Lys Leu Leu Gly Ala
        850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
                900                 905                 910
Lys Pro Tyr Asp Gly Ile Pro Ala Ser Glu Ile Ser Ser Ile Leu Glu
            915                 920                 925
Lys Gly Glu Arg Leu Pro Gln Pro Pro Ile Cys Thr Ile Asp Val Tyr
        930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                965                 970                 975
Arg Tyr Leu Val Ile Gln Gly Asp Glu Arg Met His Leu Pro Ser Pro
            980                 985                 990
```

-continued

```
Thr Asp Ser Asn Phe Tyr Arg Ala  Leu Met Asp Glu Glu  Asp Met Asp
        995                 1000              1005

Asp Val  Val Asp Ala Asp Glu  Tyr Leu Ile Pro Gln  Gln Gly Phe
    1010             1015                 1020

Phe Ser  Ser Pro Ser Thr Ser  Arg Thr Pro Leu Leu  Ser Ser Leu
    1025             1030                 1035

Ser Ala  Thr Ser Asn Asn Ser  Thr Val Ala Cys Ile  Asp Arg Asn
    1040             1045                 1050

Gly Leu  Gln Ser Cys Pro Ile  Lys Glu Asp Ser Phe  Leu Gln Arg
    1055             1060                 1065

Tyr Ser  Ser Asp Pro Thr Gly  Ala Leu Thr Glu Asp  Ser Ile Asp
    1070             1075                 1080

Asp Thr  Phe Leu Pro Val Pro  Glu Tyr Ile Asn Gln  Ser Val Pro
    1085             1090                 1095

Lys Arg  Pro Ala Gly Ser Val  Gln Asn Pro Val Tyr  His Asn Gln
    1100             1105                 1110

Pro Leu  Asn Pro Ala Pro Ser  Arg Asp Pro His Tyr  Gln Asp Pro
    1115             1120                 1125

His Ser  Thr Ala Val Gly Asn  Pro Glu Tyr Leu Asn  Thr Val Gln
    1130             1135                 1140

Pro Thr  Cys Val Asn Ser Thr  Phe Asp Ser Pro Ala  His Trp Ala
    1145             1150                 1155

Gln Lys  Gly Ser His Gln Ile  Ser Leu Asp Asn Pro  Asp Tyr Gln
    1160             1165                 1170

Gln Asp  Phe Phe Pro Lys Glu  Ala Lys Pro Asn Gly  Ile Phe Lys
    1175             1180                 1185

Gly Ser  Thr Ala Glu Asn Ala  Glu Tyr Leu Arg Val  Ala Pro Gln
    1190             1195                 1200

Ser Ser  Glu Phe Ile Gly Ala
    1205             1210
```

METHOD FOR SELECTING CHEMOTHERAPY FOR GASTRIC CANCER PATIENT USING COMBINATION DRUG OF TEGAFUR, GIMERACIL AND OTERACIL POTASSIUM AND EGFR INHIBITOR

CROSS REFERENCE TO RELATED APPLICATION

The present application is a 35 U.S.C. §371 National Phase Entry Application from PCT/JP2012/062423, filed May 15, 2012, designating the United States, which in turn claims priority to Japanese Patent Application No. 2011-109599, filed on May 16, 2011, both of which are incorporated herein by reference.

REFERENCE TO A SEQUENCE LISTING

The present application includes a Sequence Listing filed in electronic format. The Sequence Listing is entitled "2941-0208_ST25.txt" created on Dec. 12, 2013, and is 30,000 bytes in size. The information in the electronic format of the Sequence Listing is part of the present application and is incorporated herein by reference in its entirety.

TECHNICAL FIELD

The present invention relates to a method for predicting a therapeutic effect of chemotherapy that uses at least a combination drug containing tegafur, gimeracil, and oteracil potassium; an antitumor agent to be administered to a patient predicted to be likely to sufficiently respond to chemotherapy with the combination drug; a method for treating gastric cancer; and use of an antitumor agent.

BACKGROUND ART

Antitumor agents, such as 5-fluorouracil, cisplatin, irinotecan, docetaxel, a combination drug containing tegafur and uracil (product name: UFT®), a combination drug containing tegafur, gimeracil, and oteracil potassium (product name: TS-1®, hereafter, a preparation containing tegafur, gimeracil, and oteracil potassium at a molar ratio of 1:0.4:1 may be referred to as TS-1), are clinically applied in chemotherapy for advanced gastric cancer.

Meanwhile, regarding postoperative adjuvant chemotherapy for gastric cancer to prevent recurrence or metastasis after resection of gastric cancer tumor tissue, a phase III study ACTS-GC involving over 1000 patients showed that the administration of TS-1 significantly prolonged survival time both in overall survival and in relapse-free survival compared to that of the surgery-only group, and had no problems in terms of safety. Thus, the administration of TS-1 is now recognized as a standard therapy in Japan (Non-patent Literature 1).

Although postoperative adjuvant chemotherapy for gastric cancer has been intensively developed as described above, the therapeutic effect thereof is not satisfactory. In addition, since it is largely due to genetic factors of patients whether postoperative adjuvant chemotherapy is effective, there is a problem such that it is not known whether postoperative adjuvant chemotherapy is effective until an antitumor agent is actually administered.

CITATION LIST

Non-Patent Literature

NPL 1: N. Engl. J. Med. 2007; 357 (18): 1810-20.

SUMMARY OF INVENTION

Technical Problem

An object of the present invention is to provide chemotherapy that exhibits a high life-prolongation effect in gastric cancer patients, and that has fewer side effects.

Solution to Problem

The present inventors conducted extensive research on chemotherapy for gastric cancer patients and found that it can be determined by using the expression level of epidermal growth factor receptor (hereafter referred to as EGFR) as an indicator whether a combination drug containing tegafur, gimeracil, and oteracil potassium should be used in combination with an EGFR inhibitor. The present invention has been accomplished based on this finding. Although it has been reported that EGFR is associated with the therapeutic effect of a combination drug containing tegafur, gimeracil, and oteracil potassium (e.g., Oncology, 2008, 74 (1-2), 76-83), it is unknown that the expression level of EGFR can be used as an indicator when a combination drug containing tegafur, gimeracil, and oteracil potassium is used in combination with an EGFR inhibitor.

Specifically, the present invention is as follows.

Item 1. A method for predicting a therapeutic effect of chemotherapy with a combination drug containing tegafur, gimeracil, and oteracil potassium in a gastric cancer patient, the method comprising the steps of:

(1) measuring an expression level of EGFR contained in a biological sample obtained from the patient;

(2) comparing the expression level of EGFR obtained in step (1) with a corresponding predetermined cut-off point; and (3) predicting that the patient is likely to sufficiently respond to chemotherapy in which a combination drug containing tegafur, gimeracil, and oteracil potassium is used in combination with an EGFR inhibitor, when the comparison in step (2) reveals that the expression level of EGFR is greater than the cut-off point, or predicting that the patient is likely to sufficiently respond to chemotherapy in which a combination drug containing tegafur, gimeracil, and oteracil potassium is used alone, when the comparison in step (2) reveals that the expression level of EGFR is not greater than the cut-off point.

Item 2. The method of item 1, wherein the molar ratio of the respective active ingredients in the combination drug containing tegafur, gimeracil, and oteracil potassium is tegafur:gimeracil:oteracil potassium=1:0.4:1.

Item 3. The method of item 1 or 2, wherein the EGFR inhibitor is cetuximab.

Item 4. The method of any one of items 1 to 3, wherein the chemotherapy is postoperative adjuvant chemotherapy.

Item 5. An antitumor agent comprising a combination drug containing tegafur, gimeracil, and oteracil potassium and an EGFR inhibitor for use in the treatment of a gastric cancer patient predicted, according to the method of any one of items 1 to 4, to be likely to sufficiently respond to chemotherapy in which the combination drug containing tegafur, gimeracil, and oteracil potassium is used in combination with the EGFR inhibitor.

Item 6. The agent of item 5, wherein the molar ratio of the respective active ingredients in the combination drug containing tegafur, gimeracil, and oteracil potassium is tegafur:gimeracil:oteracil potassium=1:0.4:1.

Item 7. The agent of item 5 or 6, wherein the EGFR inhibitor is cetuximab.

Item 8. An antitumor agent comprising a combination drug containing tegafur, gimeracil, and oteracil potassium for use in the treatment of a gastric cancer patient predicted, according to the method of any one of items 1 to 4, to be likely to sufficiently respond to chemotherapy in which the combination drug containing tegafur, gimeracil, and oteracil potassium is used alone.

Item 9. The method of item 8, wherein the molar ratio of the respective active ingredients in the combination drug containing tegafur, gimeracil, and oteracil potassium is tegafur:gimeracil:oteracil potassium=1:0.4:1.

Item 10. A method for treating gastric cancer, comprising performing chemotherapy in which a combination drug containing tegafur, gimeracil, and oteracil potassium is used in combination with an EGFR inhibitor for a gastric cancer patient predicted, according to the method of any one of items 1 to 4, to be likely to sufficiently respond to the chemotherapy in which a combination drug containing tegafur, gimeracil, and oteracil potassium is used in combination with an EGFR inhibitor.

Item 11. A method for treating gastric cancer, comprising performing chemotherapy in which a combination drug containing tegafur, gimeracil, and oteracil potassium is used alone for a gastric cancer patient predicted, according to the method of any one of items 1 to 4, to be likely to sufficiently respond to the chemotherapy in which a combination drug containing tegafur, gimeracil, and oteracil potassium is used alone.

Item 12. Use of an antitumor agent comprising a combination drug containing tegafur, gimeracil, and oteracil potassium and an EGFR inhibitor for performing combination chemotherapy for a gastric cancer patient predicted to be likely to sufficiently respond to the combination chemotherapy according to the method of any one of items 1 to 4.

Item 13. Use of an antitumor agent comprising a combination drug containing tegafur, gimeracil, and oteracil potassium for performing chemotherapy using the combination drug alone for a gastric cancer patient predicted to be likely to sufficiently respond to the chemotherapy according to the method of any one of items 1 to 4.

Advantageous Effects of Invention

The prediction method of the present invention enables selection of chemotherapy with a superior life-prolongation effect in gastric cancer patients. More specifically, the present invention makes it possible to provide combination chemotherapy with a high life-prolongation effect in which a combination drug containing tegafur, gimeracil, and oteracil potassium and an EGFR inhibitor are used, for patients who obtain a relatively low life-prolongation effect in chemotherapy for gastric cancer using a combination drug containing tegafur, gimeracil, and oteracil potassium alone.

Additionally, gastric cancer patients who respond to chemotherapy with a combination drug containing tegafur, gimeracil, and oteracil potassium alone to a greater extent than with combination chemotherapy with a combination drug containing tegafur, gimeracil, and oteracil potassium and an EGFR inhibitor can omit the unnecessary EGFR inhibitor, thereby reducing burdens on patients. The present invention also has an advantage in terms of medical care expenses.

Figure 1:
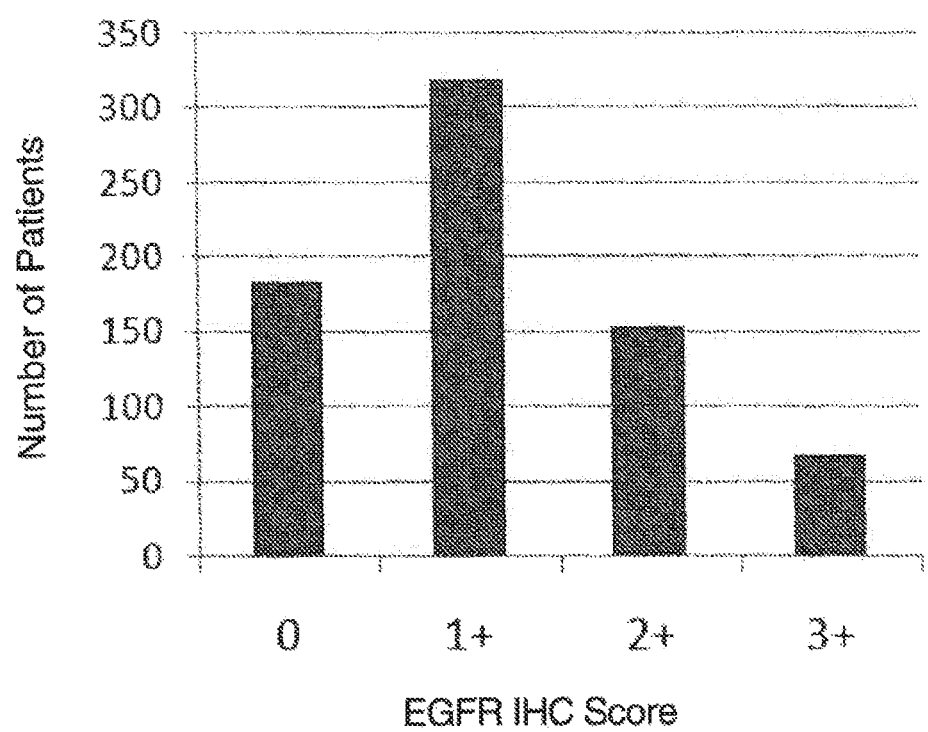
FIG. 1 shows the EGFR IHC score and the number of patients.

DESCRIPTION OF EMBODIMENTS (i) Prediction Method of the Present Invention

The prediction method of the present invention predicts whether a gastric cancer patient sufficiently responds to chemotherapy with a combination drug containing tegafur, gimeracil, and oteracil potassium, based on the expression level of EGFR of the patient.

EGFR, which is used as an indicator in the present invention, is a transmembrane tyrosine kinase receptor protein, and is known to control cell proliferation or growth by transmitting epidermal growth factor signals. The base sequence and amino acid sequence of human EGFR are registered in GenBank under the accession numbers NM005228 and NP005219, respectively. The information of these sequences can be used in the present invention. The base sequence and amino acid sequence of human EGFR in the present invention are preferably represented by SEQ ID NO: 1 and SEQ ID NO: 2, respectively, and these sequences can be used.

The target patients of the present invention are gastric cancer patients. In the present invention, "gastric cancer" includes not only primary gastric cancer, but also locally recurrent gastric cancer and metastatic gastric cancer that has spread to other tissue (e.g., lymph node). The gastric cancer is preferably primary gastric cancer. The gastric cancer patients include not only patients having gastric cancer tumor tissue, but also patients who have undergone resection of gastric cancer tumor tissue.

"Combination drug containing tegafur, gimeracil, and oteracil potassium" in the present invention means a combination drug containing three pharmaceutical agents, i.e., tegafur, gimeracil, and oteracil potassium. "Tegafur" (generic name, chemical name: 5-fluoro-1-(2-tetrahydrofuryl)-2,4-(1H,3H)-pyrimidinedione) is a known compound and a drug that is activated in vivo to release 5-fluorouracil, which is a substance responsible for antitumor activity. Tegafur can be produced according to a known method, such as the method disclosed in JP49-010510B.

"Gimeracil" (generic name, chemical name: 2,4-dihydroxy-5-chloropyridine) is also a known compound. Although gimeracil itself does not exhibit antitumor activity, it can inhibit metabolic inactivation of 5-fluorouracil in vivo, thereby potentiating the antitumor effect.

"Oteracil potassium" (generic name, chemical name: monopotassium 1,2,3,4-tetrahydro-2,4-dioxo-1,3,5-triazine-6-carboxylate) is also a known compound. Although oteracil potassium itself does not exhibit antitumor activity, it is chiefly distributed in the gastrointestinal tract, where it inhibits the activation of 5-fluorouracil, thereby preventing gastrointestinal tract disorders.

The proportion of each active ingredient of the "combination drug containing tegafur, gimeracil, and oteracil potassium" in the present invention is not particularly limited, as long as the purpose of each active ingredient is achieved. For example, the proportion of each active ingredient may be within the same range as that in the known combination drug disclosed in JP2614164B. The proportion is usually such that, per mole of tegafur, gimeracil is used in a proportion of about 0.1 to about 5 moles, and preferably about 0.2 to about 1.5 moles, and oteracil potassium is used in a proportion of about 0.1 to about 5 moles, and preferably about 0.2 to about 2 moles. It is particularly preferred that the molar ratio of tegafur:gimeracil:oteracil potassium is 1:0.4:1. A combination drug containing tegafur, gimeracil, and oteracil potassium at a molar ratio of 1:0.4:1 is available under the name "TS-1" (product name, Taiho Pharmaceutical Co., Ltd.).

The "EGFR inhibitor" of the present invention is not particularly limited as long as it is a drug that inhibits the expression or activity of EGFR. The EGFR inhibitor may be a low-molecular compound that targets EGFR, such as gefitinib and erlotinib; an anti-EGFR antibody, such as cetuximab and panitumumab; an antisense oligonucleotide to EGFR; an aptamer to EGFR; or the like. Of these, anti-EGFR antibodies are preferable, and cetuximab is particularly preferable.

"Cetuximab" is a human/mouse chimeric monoclonal antibody that specifically recognizes EGFR, and is known to inhibit the activation and dimerization of EGFR, thereby exhibiting a tumor growth inhibitory effect on colorectal cancer, head and neck cancer, non small-cell lung cancer, gastric cancer, etc. Cetuximab can be produced by a known method, such as the method disclosed in JP06-051689B.

The combination drug containing tegafur, gimeracil, and oteracil potassium and the EGFR inhibitor may be provided as a combination drug (preparation containing a plurality of active ingredients) by formulating tegafur, gimeracil, oteracil potassium and the EGFR inhibitor into a single dosage form (single-formulation type); or may be provided as single active ingredient preparations by formulating the active ingredients into a plurality of dosage forms (multiple-formulation type). Of these, preferable is a multiple-formulation type in which tegafur, gimeracil, and oteracil potassium are formulated as a combination drug and the EGFR inhibitor is formulated as a single active ingredient preparation.

The dosage form of the antitumor agents is not particularly limited, and can be suitably selected depending on the purpose of the treatment. Specific examples thereof include oral preparations (such as tablets, coated tablets, powders, granules, capsules, and fluids), injections, suppositories, patches, and ointments. Of these, an oral preparation is preferable as the dosage form of the combination drug containing tegafur, gimeracil, and oteracil potassium. Each antitumor agent can be prepared by a commonly known method, using one or more pharmacologically acceptable carriers in accordance with each dosage form. Examples of the carriers include those that are widely used in common drugs, such as excipients, binders, disintegrators, lubricants, diluents, solubilizing agents, suspending agents, tonicity adjusting agents, pH adjusters, buffers, stabilizers, colorants, sweetening agents, and flavoring agents.

"Chemotherapy with a combination drug containing tegafur, gimeracil, and oteracil potassium" in the present invention means chemotherapy in which at least the combination drug containing tegafur, gimeracil, and oteracil potassium is administered; and includes not only chemotherapy in which the combination drug containing tegafur, gimeracil, and oteracil potassium is used alone, but also chemotherapy in which the combination drug containing tegafur, gimeracil, and oteracil potassium is used in combination with other antitumor agents.

"Chemotherapy in which a combination drug containing tegafur, gimeracil, and oteracil potassium is used in combination with an EGFR inhibitor" means chemotherapy in which the combination drug containing tegafur, gimeracil, and oteracil potassium and the EGFR inhibitor are administered in combination, and more preferably chemotherapy in which the combination drug containing tegafur, gimeracil, and oteracil potassium at a molar ratio of 1:0.4:1 and cetuximab are administered in combination. These drugs may be administered simultaneously or at different dates and times, as long as the effect achieved by the combined use can be obtained.

The administration schedule in the "chemotherapy in which a combination drug containing tegafur, gimeracil, and oteracil potassium is used alone" of the present invention is suitably selected according to conditions such as patient's age, sex, stage of disease, presence or absence of metastasis, and history of treatment. Examples thereof include the following administration schedule. The combination drug containing tegafur, gimeracil, and oteracil potassium (molar ratio of tegafur:gimeracil:oteracil potassium=1:0.4:1) is administered every day for 4 weeks in an amount of 80 mg/m$^2$ (in terms of tegafur, per body surface area)/day, followed by 2-week withdrawal. These 6 weeks are regarded as one course, and this course is repeated one or more times.

The administration schedule in the "chemotherapy in which a combination drug containing tegafur, gimeracil, and oteracil potassium is used in combination with an EGFR inhibitor" of the present invention is suitably selected according to conditions such as the patient's age, sex, stage of disease, presence or absence of metastasis, and history of treatment. Examples thereof include the following administration schedule. The combination drug containing tegafur, gimeracil, and oteracil potassium (molar ratio of tegafur:gimeracil:oteracil potassium=1:0.4:1) is administered every day for 4 weeks in an amount of 80 mg/m$^2$ (in terms of tegafur, per body surface area)/day, followed by 2-week withdrawal; cetuximab is administered weekly in an amount of 250 mg/m$^2$ (per body surface area) (a total of 6 times). These 6 weeks are regarded as one course, and this course is repeated one or more times (however, the dose of cetuximab on the first day of each course is 400 mg/m$^2$ (per body surface area)).

The chemotherapy of the present invention may be preoperative adjuvant chemotherapy in which tumor is removed after the chemotherapy is performed, or postoperative adjuvant chemotherapy in which the combination chemotherapy is performed after removal of tumor.

In the present invention, "therapeutic effect" can be evaluated by a tumor-shrinking effect, an effect of prolonging survival time, etc. Survival time can be represented by the median of overall survival or progression-free survival; or the like. "Sufficiently respond to chemotherapy in which a combination drug containing tegafur, gimeracil, and oteracil potassium is used in combination with an EGFR inhibitor" indicates a condition in which a patient responds to chemotherapy in which the combination drug containing tegafur, gimeracil, and oteracil potassium is used in combination with the EGFR inhibitor to a greater extent than with chemotherapy in which the combination drug containing tegafur, gimeracil, and oteracil potassium is used alone. "Sufficiently respond to chemotherapy in which a combination drug containing tegafur, gimeracil, and oteracil potassium is used alone" indicates a condition in which a patient responds to chemotherapy in which the combination drug containing tegafur, gimeracil, and oteracil potassium is used alone to a greater extent than with chemotherapy in which the combination drug containing tegafur, gimeracil, and oteracil potassium is used in combination with the EGFR inhibitor.

The prediction method of the present invention comprises steps (1) to (3) described below.

Step (1) is a step of measuring the expression level of EGFR contained in a biological sample obtained from a patient.

The biological sample is not particularly limited, as long as it is obtained from a cancer patient and contains cancer cells. Examples thereof include body fluid (such as blood and urine), tissue, extracts thereof, and cultures of obtained tissue. The method for obtaining the biological sample can be suitably selected according to the type of biological sample.

The expression level of EGFR in the present invention may be the mRNA expression level or the protein expression level. From the viewpoint of convenience of measurement, etc., the protein expression level is preferable.

The measurement method of the present invention is not particularly limited as long as it can quantify the amount of mRNA or protein, and a known measurement method can be used. Examples of methods for measuring the amount of mRNA include the PCR method, the RT-PCR method, the northern blotting method, the fluorescence in situ hybridization method (FISH method), the microarray method, and the like. Examples of methods for measuring the amount of protein include the western blotting method, the immunohistochemical staining method (IHC method), and the like. Of these, the IHC method is preferable from the viewpoint of convenience, etc. The IHC method is a commonly used measurement method that can evaluate the amount of protein using an anti-EGFR antibody by giving a score on a 4-point scale, i.e., 0 to 3+, based on the staining intensity of tumor cells and the percentage of positive cells (Cancer, 2001, 92 (5): 1331-46; Lung Cancer, 2010, 68 (3): 375-82).

The biological sample is prepared by being subjected to a process appropriate for each of the above measurement methods. As a reagent used for the measurement that comprises one or more primers, probes, or antibodies, the below-described reagent of the present invention can be used.

Step (2) is a step of comparing the expression level of EGFR obtained in step (1) with a corresponding predetermined cut-off point.

Cut-off points can be determined from previously measured expression levels of EGFR by using various statistical analysis techniques. Examples of such cut-off points include the following values.

1. Average or median value of EGFR expression levels of gastric cancer patients;
2. Value determined based on Receiver Operating Characteristic (ROC) analysis such that the sum of sensitivity and specificity is maximum from the relevance between EGFR expression levels of gastric cancer patients and predetermined therapeutic effect. ROC analysis, which is frequently used for clinical laboratory diagnosis, is an analysis technique that determines a threshold value at which the sum of sensitivity and specificity is maximum.

More specifically, as described in detail in the below-described Examples, when the expression level of EGFR protein is measured by, for example, the IHC method, the cut-off point of EGFR is preferably 0 to 2+, and particularly preferably 1+, based on the above-described calculation method for cut-off points.

Step (3) is a step of predicting that the patient is likely to sufficiently respond to chemotherapy in which the combination drug containing tegafur, gimeracil, and oteracil potassium is used in combination with the EGFR inhibitor, when the comparison in step (2) reveals that the expression level of EGFR is greater than the cut-off point, or predicting that the patient is likely to sufficiently respond to chemotherapy in which the combination drug containing tegafur, gimeracil, and oteracil potassium is used alone, when the comparison in step (2) reveals that the expression level of EGFR is not greater than the cut-off point.

(ii) Reagent of the Present Invention

The reagent of the present invention is a reagent for use in the above-described prediction method of the present invention, and comprises one or more primers or probes that specifically hybridize with EGFR mRNA, or one or more antibodies that specifically recognize EGFR protein.

The primer or probe of the present invention comprises a polynucleotide that has a base sequence of not less than 15 bases and that specifically hybridizes with a continuous base sequence of at least 15 bases of the base sequence shown in SEQ ID NO: 1. Although the sequence length of the primer or probe is not less than 15 bases, the primer or probe is not particularly limited as long as it specifically hybridizes with EGFR mRNA.

Here, specific hybridization refers to hybridization that forms a specific hybrid and does not form a nonspecific hybrid under stringent hybridization conditions. The stringent hybridization conditions can be determined by an ordinary method, for example, based on the melting temperature (Tm) of the nucleic acid at which the hybrid is formed. A specific cleaning condition to maintain the hybridization conditions is commonly about "1×SSC, 0.1% SDS, 37° C.," more strictly about "0.5×SSC, 0.1% SDS, 42° C.," and still more strictly about "0.1×SSC, 0.1% SDS, 65° C."

The polynucleotide preferably has a base sequence that is complementary to a continuous base sequence of at least 15 bases of the base sequence shown in SEQ ID NO: 1; however, the polynucleotide is not required to be fully complementary to the continuous base sequence as long as the specific hybridization is possible. The polynucleotide has an identity of not less than 70%, preferably not less than 80%, more preferably not less than 90%, yet more preferably not less than 95%, and still more preferably not less than 98%, with respect to the polynucleotide comprising a continuous base sequence of at least 15 bases of the base sequence shown in SEQ ID NO: 1, or the complementary polynucleotide thereof. The identity of the base sequence can be calculated by way of an identity search, sequence alignment program, BLAST, FASTA, ClustalW, or the like.

Such polynucleotides can be prepared by an ordinary method, for example, using a commercially available nucleotide synthesizer, based on the total base length of the base sequence shown in SEQ ID NO: 1. The polynucleotides can also be prepared by the PCR method, using the total base length of the base sequence shown in SEQ ID NO: 1 as a template.

The antibody of the present invention is not particularly limited as long as it recognizes a polypeptide comprising the amino acid sequence shown in SEQ ID NO: 2. The antibody may be either a monoclonal antibody or a polyclonal antibody; or an antibody fragment, such as Fab, F(ab')2, Fab', scFV, diabody, dsFv, and a CDR-containing polypeptide. The antibody may be prepared using, as an immunogen, a polypeptide comprising the amino acid sequence shown in SEQ ID NO: 2 or may be an antibody with antigen binding to a polypeptide comprising at least 8 continuous amino acids, preferably at least 15 continuous amino acids, and more preferably at least 20 continuous amino acids, of an amino acid sequence constituting a polypeptide comprising the amino acid sequence shown in SEQ ID NO: 2. Such polypeptides can be commonly synthesized by a known method based on the amino acid sequence shown in SEQ ID NO: 2 or a base sequence encoding the amino acid sequence shown in SEQ ID NO: 2. Examples of such methods include chemical synthesis techniques with an amino acid synthesizer and genetic engineering techniques.

The antibody of the present invention can be produced by an ordinary method (e.g., Current Protocols in Molecular Biology, Edit, Ausubel et al, (1987), Publish, John Wiley & Sons. Sections 11.12-11.13), For example, when the antibody of the present invention is a polyclonal antibody, it can be obtained by immunizing a test animal with the aforementioned polypeptide expressed in E. coli and purified by an ordinary method, or a polypeptide synthesized so as to have a partial amino acid sequence of the aforementioned polypeptide by an ordinary method; and obtaining the antibody from the serum of the immunized animal by an ordinary method. For example, when the antibody of the present invention is a monoclonal antibody, it can be obtained by immunizing a test animal with the aforementioned polypeptide expressed in E. coli, etc., and purified by an ordinary method, or a polypeptide synthesized so as to have a partial amino acid sequence of the aforementioned polypeptide by an ordinary method; fusing the spleen cell obtained from the test animal and a myeloma cell to synthesize a hybridoma cell; and obtaining the antibody from the hybridoma cell.

EXAMPLES

Examples are given below to illustrate the present invention in more detail. Needless to say, the present invention is not limited to these Examples.

Example 1

EGFR Expression Levels in Gastric Cancer Patients

Patients with stage II to III gastric cancer (1059 patients) were divided into a surgery-only group and a TS-1 treatment group after resection of gastric cancer tumor tissue. TS-1 was administered to the TS-1 treatment group every day for 4 weeks in an amount of 80 to 120 mg/day (in terms of tegafur, body surface area of less than 1.25 $m^2$: 80 mg/day; body surface area of not less than 1.25 $m^2$ to less than 1.5 $m^2$: 100 mg/day; body surface area of not less than 1.5 $m^2$: 120 mg/day), followed by a 2-week withdrawal. These 6 weeks were regarded as one course. This course was repeated for 1 year after surgery.

Figure 2:
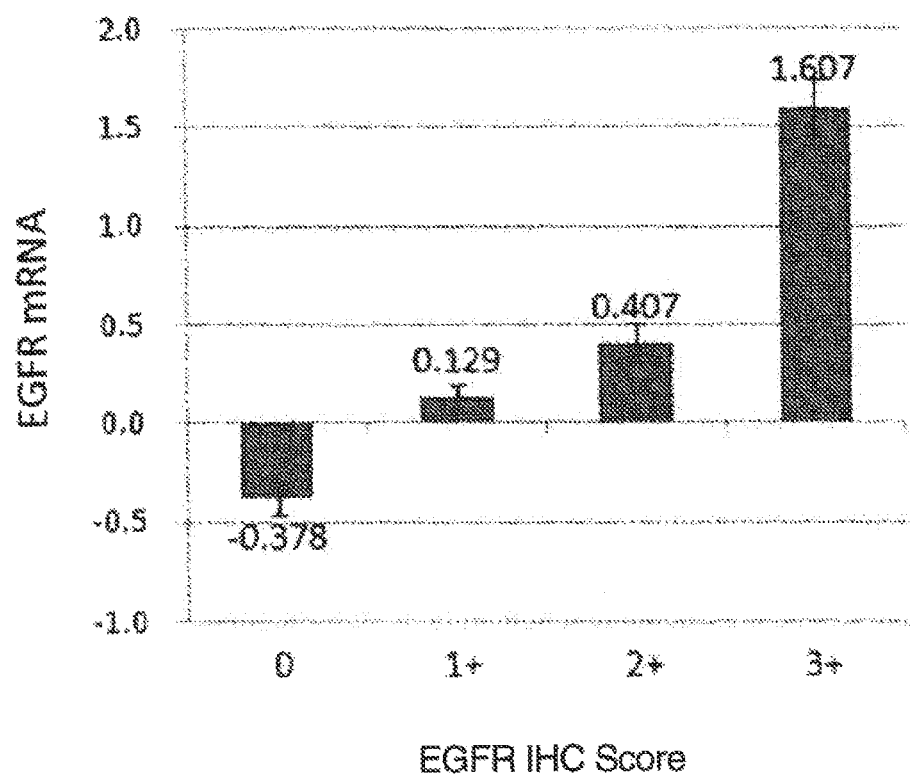
FIG. 2 shows the EGFR IHC score and the expression level of EGFR mRNA (EGFR/ACTB, log 2-transformed value).

In 753 patients among all the patients, formalin-fixed paraffin-embedded pathological samples were successfully prepared from surgically removed gastric cancer tumor tissue. From the paraffin-embedded pathological samples, the expression levels of EGFR protein were measured by the IHC method, and the expression levels of EGFR mRNA were measured by the TaqMan PCR method. FIG. 1 shows the EGFR IHC score and the number of patients. FIG. 2 shows the EGFR IHC score and the expression level of EGFR mRNA (EGFR/ACTB, log 2-transformed value).

Figure 3:
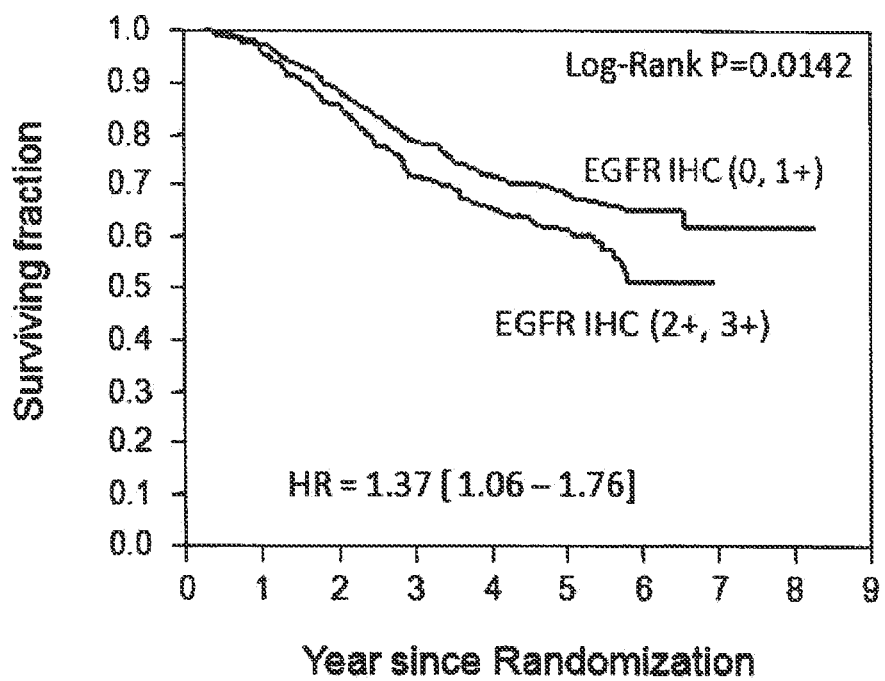
FIG. 3 shows Kaplan-Meier survival curves in a high EGFR expression group and a low EGFR expression group.

Thereafter, based on the EGFR INC scores (0, 1+, 2+, 3+), 1+ was defined as a cut-off point. The patients with the score (0, 1+) were classified as a low EGFR expression group (526 patients), and the patients with the score (2+, 3+) were classified as a high EGFR expression group (227 patients). Survival analysis was performed using overall survival in each group. FIG. 3 shows Kaplan-Meier survival curves in the high EGFR expression group and the low EGFR expression group.

A log-rank test performed for the overall survival in the high EGFR expression group and the low EGFR expression group revealed that the p-value was significant, i.e., 0.0142. In univariate analysis using a Cox hazards model, the hazard ratio of the high EGFR expression group to the low EGFR expression group was 1.37, indicating that the high EGFR expression group had a significantly poor prognosis compared to that of the low EGFR expression group. EGFR was also an independent poor prognostic factor in multivariate analysis adjusting for sex, age, stage, and TNM classification. Regardless of the high EGFR expression group or the low EGFR expression group, both the overall survival and relapse-free survival were significantly prolonged in the TS-1 treatment group compared to those of the surgery-only group.

The above results proved that, although chemotherapy using TS-1 is clinically useful for gastric cancer patients regardless of EGFR expression, the chemotherapy exhibits a highly superior therapeutic effect, in particular, in gastric cancer patients with low expression levels of EGFR.

Example 2

Next, an in vivo efficacy test was performed in human gastric cancer strain subcutaneously implanted into nude mice to verify the usefulness of new combination chemotherapy for gastric cancer. SC-4 tumors derived from human gastric cancer were subcutaneously implanted in nude mice by an ordinary method. TS-1 was orally administered every day from day 1 to day 14 at three different doses at a common ratio of 1.2 from 10 mg/kg/day (10, 8.3, and 6.9). Cetuximab was intraperitoneally administered at a dose of 20 mg/kg on day 1, day 4, day 8, and day 11. In addition, both of the drugs were used in combination at the same doses, administration routes, and administration schedules as when each drug was used alone. The major axis and minor axis of each tumor were measured daily with a digital vernier caliper to calculate the tumor volume. At the same time, the body weight was measured as an indicator of side effects. The reduction ratio of the tumor volume of each drug-treated group to the tumor volume of the non-drug-treated control group (Relative Tumor Volume, RTV) was calculated, and regarded as in vivo efficacy.

Figure 4:
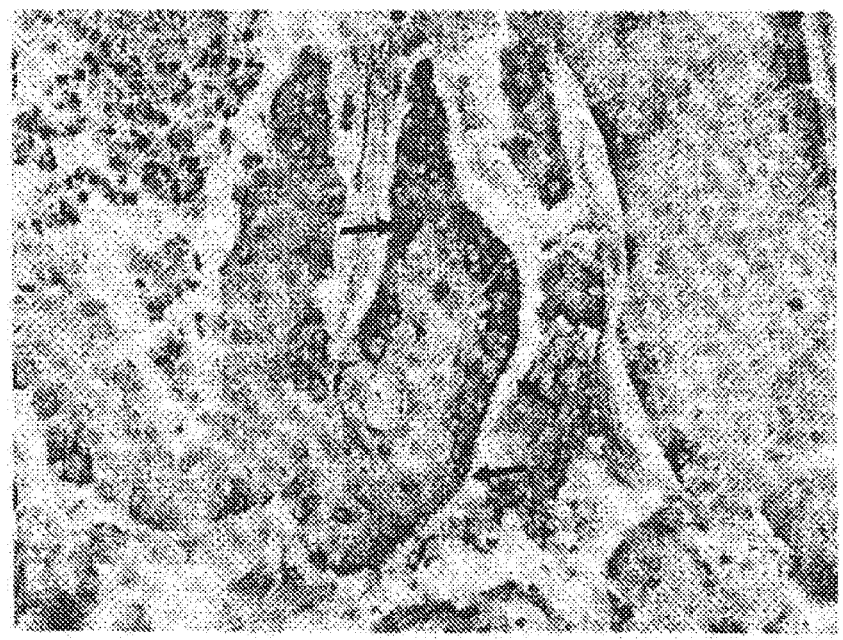
FIG. 4 is an image of SC-4 gastric cancer strain by the IHC method (EGFR positive cells (arrows), ×400).

The EGFR expression level in the strain SC-4 derived from human gastric cancer was measured by the TaqMan PCR method. The measurement confirmed that the value thereof was 1.66 (EGFR/ACTB, log 2-transformed value) and that the SC-4 was a highly EGFR-expressing strain that corresponds to an IHC score of not less than 2+. Further, the expression level of EGFR protein in the SC-4 was measured by the immunohistochemical staining method (IHC method). The measurement using the IHC method was performed by deparaffinizing Carnoy-fixed paraffin-embedded thin sections of the SC-4, blocking endogenous peroxidase with Dako Real Peroxidase-Blocking Solution, performing a primary antibody reaction (anti-human EGFR mouse monoclonal antibody (clone No. 2-18C9; produced by Dako)), performing a secondary antibody reaction using a polymer reagent (Labeled Polymer-HRP; produced by Dako), and developing color with a chromogenic substrate (3 3'-diaminobenzidine tetrahydrochloride+chromogen; produced by Dako). FIG. 4 shows the results. The IHC method also confirmed that the SC-4 was a highly EGFR-expressing strain that corresponds to an IHC score of not less than 2+.

Figure 5:
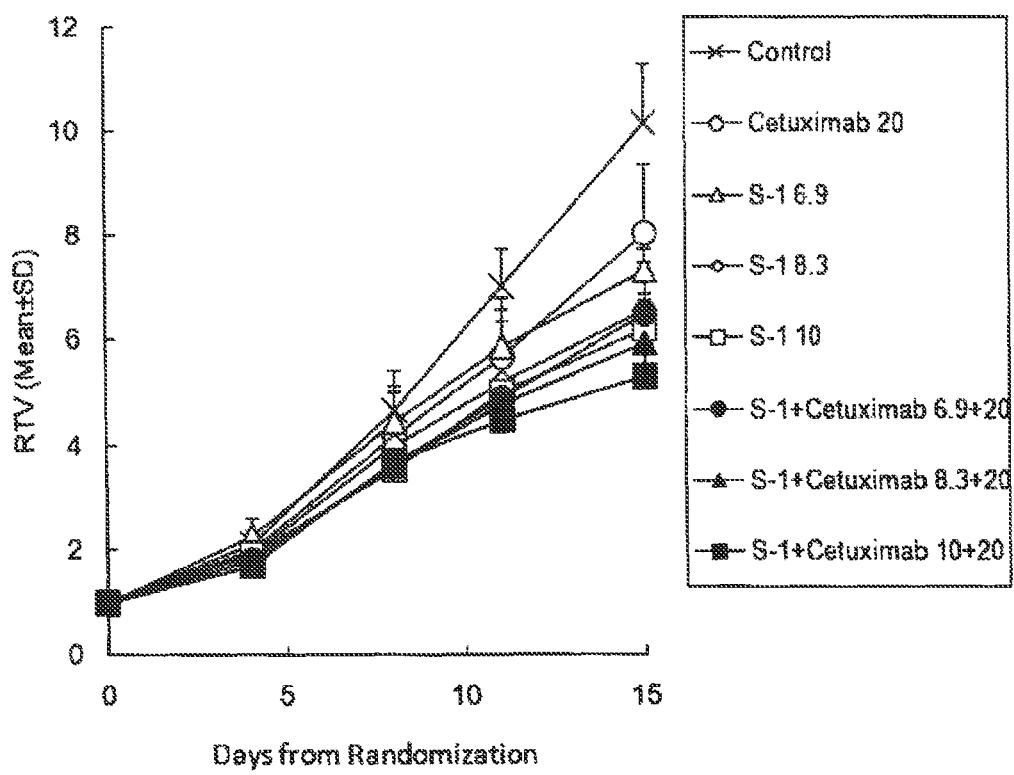
FIG. 5 is a graph showing the change in the tumor volume per day obtained using SC-4 gastric cancer strain.
Figure 6:
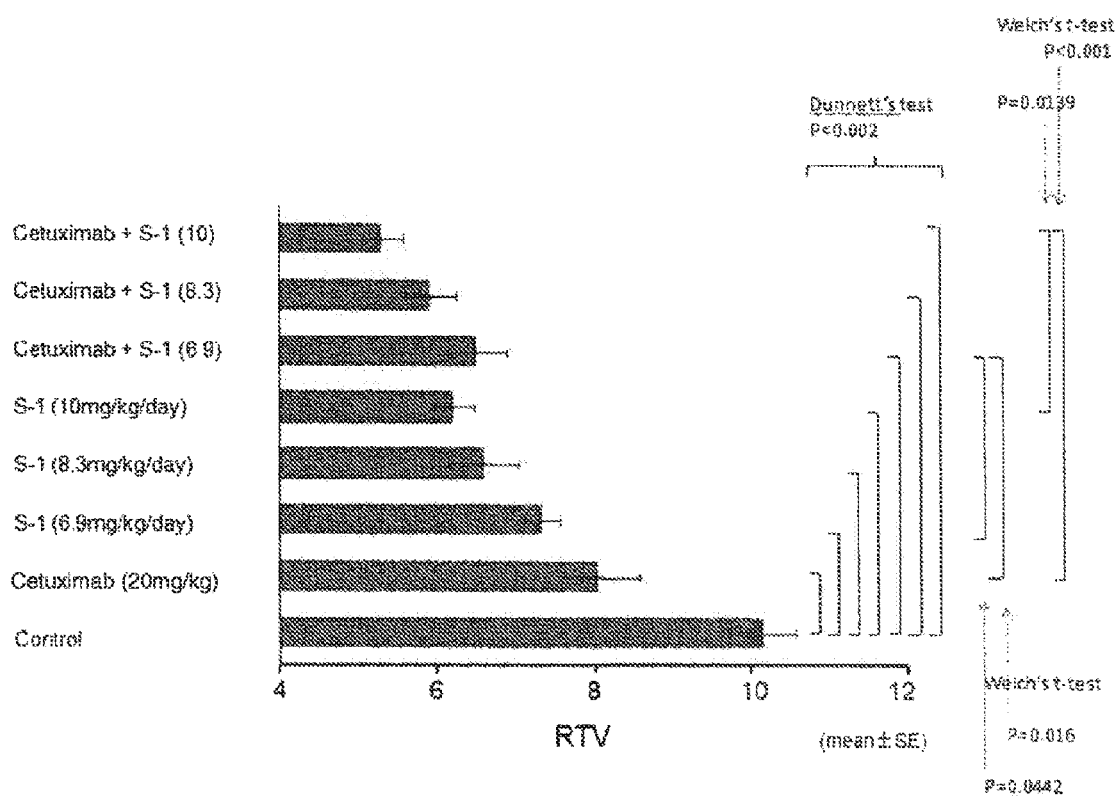
FIG. 6 is a graph of RTV on day 15, the final effect determination day, with the IUT test results according to the IUT procedure.

The tumor growth inhibitory effect was 39% in the administration of TS-1 alone at 10 mg/kg/day and 21% in the administration of cetuximab alone. On the other hand, it was confirmed that the combined use of these drugs potentiated the tumor growth inhibitory effect, i.e. 48%. The efficacy of each drug alone and the efficacy of the combined use were statistically tested according to the Intersection-Union Test (IUT) procedure, and the significance of the combined use was confirmed. Similarly, the significance of effect of the combined use of TS-1 at 6.9 mg/kg/day and cetuximab at 20 mg/kg/day was also confirmed by the IUT procedure: 28% in the administration of TS-1 at 6.9 mg/kg/day and 36% in the combined use with cetuximab at 20 mg/kg/day. Examination of side effects using the body weight as an indicator showed that the body weight decrease in the cetuximab and TS-1 combination group was below 16%, which is well within the allowable range. FIG. 5 is a graph showing the change in the tumor volume per day. FIG. 6 is a graph of RTV on day 15, the final effect determination day, with the IUT test results according to the IUT procedure.

Example 3

Next, an in vivo efficacy test was performed in SC-2 gastric cancer strain subcutaneously implanted into nude mice to verify reproducibility of the results obtained using the SC-4 gastric cancer strain. SC-2 tumors derived from human gastric cancer were subcutaneously implanted in nude mice by an ordinary method. TS-1 was orally administered every day from day 1 to day 14 at three different doses, at a common ratio of 1.2 from 10 mg/kg/day (10, 8.3, and 6.9). Cetuximab was intraperitoneally administered at a dose of 20 mg/kg on day 1, day 4, day 8, and day 11. In addition, both of the drugs were used in combination at the same doses, administration routes, and administration schedules as when each drug was used alone. The major axis and minor axis of each tumor was measured daily with a digital vernier caliper to calculate the tumor volume. At the same time, the body weight was measured as an indicator of side effects. The reduction ratio of the tumor volume of each drug-treated group to the tumor volume of the non-drug-treated control group (Relative Tumor Volume, RTV) was calculated and regarded as in vivo efficacy.

Figure 7:
FIG. 7 is an image of SC-2 gastric cancer strain by the IHC method (EGFR positive cells (arrows), ×400).

The EGFR expression level in the strain SC-2 derived from human gastric cancer was measured by the TaqMan PCR method. The measurement confirmed that the value thereof was 0.93 (EGFR/ACTB, log 2-transformed value) and that the SC-2 was a highly EGFR-expressing strain that corresponded to an IHC score of not less than 2+. Further, as in Example 2, the expression level of EGFR protein was measured by the IHC method. The measurement confirmed that the SC-2 was a highly EGFR-expressing strain that corresponded to an IHC score of not less than 2+(FIG. 7).

Figure 8:
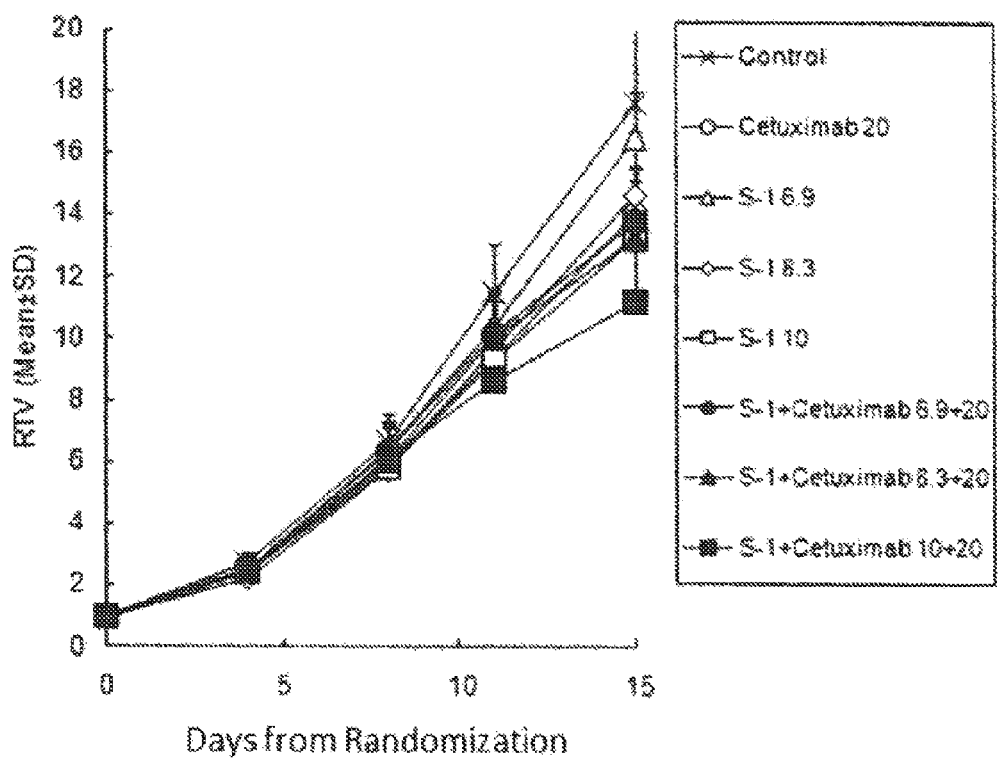
FIG. 8 is a graph showing the change in the tumor volume per day obtained using SC-2 gastric cancer strain.
Figure 9:
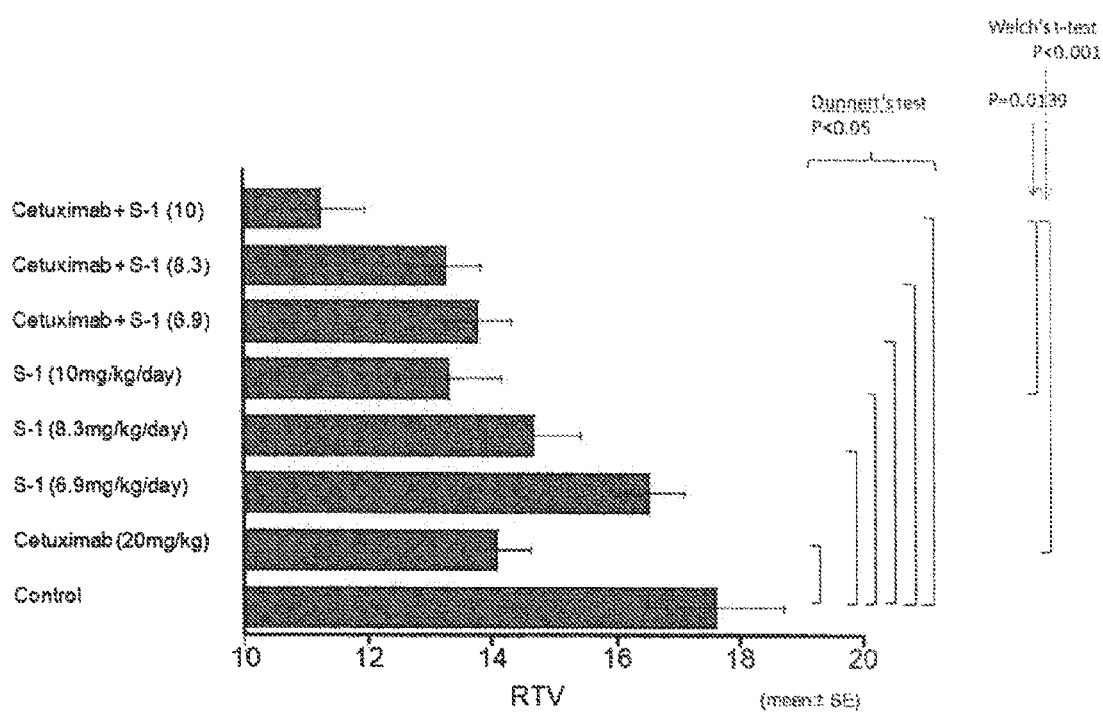
FIG. 9 is a graph of RTV on day 15, the final effect determination day, with the IUT test results according to the IUT procedure.

The tumor growth inhibitory effect was 25% in the administration of TS-1 alone at 10 mg/kg/day, and 20% in the administration of cetuximab alone. On the other hand, it was confirmed that the combined use of these drugs potentiated the tumor growth inhibitory effect, i.e., 36%. The efficacy of each drug alone and the efficacy of the combined use were statistically tested according to the Intersection-Union Test (IUT) procedure, and the significance of the combined use was confirmed. Examination of side effects using the body weight as an indicator showed that the body weight decrease in the cetuximab and TS-1 combination group was below 8%, which is well within the allowable range. FIG. 8 is a graph showing the change in the tumor volume per day. FIG. 9 is a graph of RTV on day 15, the final effect determination day, with the IUT test results according to the IUT procedure.

A significant effect of the combined use was confirmed in the highly EGFR-expressing SC-2 and SC-4. This indicates that chemotherapy using TS-1 in combination with cetuximab is useful for gastric cancer patients with high expression levels of EGFR.

The above results found that EGFR is a poor prognostic factor in chemotherapy with a combination drug containing tegafur, gimeracil, and oteracil potassium for gastric cancer patients. Further, a significant effect of the combined use of cetuximab and TS-1 was confirmed in the highly EGFR-expressing gastric cancer strains, indicating that individualized therapy for gastric cancer that uses EGFR as a biomarker and that comprises a combination drug containing tegafur, gimeracil, and oteracil potassium is possible.

The invention claimed is:

1. A method for treating gastric cancer in a patient in need of such treatment, comprising:
   (1) measuring an expression level of EGFR contained in a biological sample obtained from the patient with an immunohistochemical staining method (IHC method);
   (2) comparing the expression level of EGFR obtained in step (1) with a corresponding predetermined cut-off point, wherein the corresponding predetermined cut-off point of the expression level of EGFR protein is 1+; and
   (3) thereafter performing chemotherapy by administering a combination drug containing tegafur, gimeracil, and oteracil potassium in combination with an EGFR inhibitor to said patient when the comparison in step (2) reveals that the expression level of EGFR is greater than the cut-off point.

2. A method for treating gastric cancer in a patient in need of such treatment, comprising:
   (1) measuring an expression level of EGFR contained in a biological sample obtained from the patient with an immunohistochemical staining method (IHC method);
   (2) comparing the expression level of EGFR obtained in step (1) with a corresponding predetermined cut-off point, wherein the corresponding predetermined cut-off point of the expression level of EGFR protein is 1+; and
   (3) thereafter performing chemotherapy by administering a combination drug containing tegafur, gimeracil, and oteracil potassium alone to said patient when the comparison in step (2) reveals that the expression level of EGFR is not greater than the cut-off point.

3. The method according to claim 1, wherein the combination drug containing tegafur, gimeracil, and oteracil potassium has a molar ratio for tegafur:gimeracil:oteracil potassium=1:0.4:1.

4. The method according to claim 1, wherein the EGFR inhibitor is cetuximab.

5. The method according to claim 1, wherein the chemotherapy is postoperative adjuvant chemotherapy.

6. The method according to claim 2, wherein the combination drug containing tegafur, gimeracil, and oteracil potassium has a molar ratio for tegafur:gimeracil:oteracil potassium=1:0.4:1.

7. The method according to claim 2, wherein the chemotherapy is postoperative adjuvant chemotherapy.

8. The method according to claim 1, wherein the combination drug containing tegafur, gimeracil, and oteracil potassium, and the EGFR inhibitor used in combination are administered according to an administration schedule of one or more 6 week courses, the 6 week course comprising:
   administering the combination drug every day for 4 weeks in an amount of 80 mg/m$^2$, in terms of tegafur per body surface area, per day, followed by 2-week withdrawal, and administering the EGFR inhibitor weekly in an amount of 400 mg/m$^2$ per body surface area on the first day of each course and 250 mg/m$^2$ per body surface area on the remaining days.

9. The method according to claim 2, wherein the combination drug containing tegafur, gimeracil, and oteracil potassium is administered according to an administration schedule of one or more 6 week courses, the 6 week course comprising:

administering the combination drug every day for 4 weeks in an amount of 80 mg/m$^2$, in terms of tegafur per body surface area, per day, followed by 2-week withdrawal.

* * * * *